United States Patent
Contadini et al.

(10) Patent No.: US 6,267,297 B1
(45) Date of Patent: Jul. 31, 2001

(54) PROGRAMMABLE DISPENSER

(75) Inventors: Carl D. Contadini, Terryville; Nicholas A. Velezis, Middlebury; John J. Dean, Oxford, all of CT (US)

(73) Assignee: Waterbury Companies, Inc., Waterbury, CT (US)

( * ) Notice: Subject to any disclaimer, the term of this patent is extended or adjusted under 35 U.S.C. 154(b) by 0 days.

(21) Appl. No.: 09/415,840

(22) Filed: Oct. 12, 1999

(51) Int. Cl.⁷ ............................. B05B 17/00; A01G 27/00
(52) U.S. Cl. ....................... 239/1; 239/69; 239/70; 239/71; 239/99; 239/326; 239/333; 239/337; 222/646; 222/649
(58) Field of Search ................... 239/69, 70, 67, 239/71, 72, 74, 99, 302, 326, 274, 333, 332, 337, 350, 351, 1, 11; 222/642, 61, 63, 645, 649, 162; 340/333; 137/78

(56) References Cited

U.S. PATENT DOCUMENTS

| | | |
|---|---|---|
| 3,589,563 | 6/1971 | Carragan et al. . |
| 4,007,755 | 2/1977 | Lerner et al. . |
| 4,063,664 | 12/1977 | Meetze, Jr. . |
| 4,415,797 * | 11/1983 | Choustoulakis ................ 239/70 X |
| 4,658,985 | 4/1987 | Madsen et al. . |
| 4,671,435 * | 6/1987 | Stout et al. ..................... 239/69 X |
| 4,707,338 | 11/1987 | Spector . |
| 4,760,547 * | 7/1988 | Duxbury ......................... 239/69 X |
| 4,830,791 | 5/1989 | Muderlak et al. . |
| 5,038,972 | 8/1991 | Muderlak et al. . |
| 5,126,078 | 6/1992 | Steiner et al. . |
| 5,249,718 * | 10/1993 | Muderlak ........................ 239/70 X |
| 5,370,829 | 12/1994 | Kunze . |
| 5,772,074 | 6/1998 | Dial et al. . |
| 5,884,808 | 3/1999 | Muderlak et al. . |
| 6,039,212 * | 3/2000 | Singh ........................... 222/646 X |

* cited by examiner

Primary Examiner—David A. Scherbel
Assistant Examiner—Steven J. Ganey
(74) Attorney, Agent, or Firm—Carmody & Torrance LLP (57) ABSTRACT

A programmable dispenser, especially for dispensing an olfactory stimulating material from a source of the material, is presented. More particularly, the present invention relates to a dispenser for an olfactory stimulating material, such as an air freshener composition, wherein the dispenser can be programmed so as to be operational within a wide variety of operating modes, such as starting and ending operations at specific times during the day, being operational during specific days of the week, and dispensing frequency (i.e., in the case of an aerosol or pump source) and/or intensity (i.e., in the case of a gel or cartridge source).

12 Claims, 7 Drawing Sheets

PROGRAMMABLE DISPENSER

TECHNICAL FIELD

A programmable dispenser, especially for dispensing an olfactory stimulating material from a source of the material, is presented. More particularly, the present invention relates to a dispenser for an olfactory stimulating material, such as an air freshener composition, wherein the dispenser can be programmed so as to be operational within a wide variety of operating modes, such as starting and ending operations at specific times during the day, being operational during specific days of the week, and dispensing frequency (i.e., in the case of an aerosol or pump source) and/or intensity (i.e., in the case of a gel or cartridge source).

Dispensers which provide an olfactory stimulating material, such as an air freshener composition, are known, and often disposed, inter alia, in public rest rooms. Such dispensers provide to the surrounding atmosphere an olfactory stimulating material from a refill or other source of olfactory stimulating material. Since the need for air freshening varies widely, depending on the application, dispensers which cannot be programmed with wide flexibility are either operating even when the need for freshening is not great, resulting in waste, or operating with insufficient frequency or intensity when the need is greatest, resulting in insufficient air freshening. For instance, an air freshening dispenser mounted in a public restroom in an office building should be operational during normal business hours, such as 8:00 a.m. to 7:00 p.m., but not earlier or later since the need for air freshening is not great outside of those weekday hours. Similarly, even if the office building is occupied on weekends, the hours of operation and the frequency and/or intensity of dispensing should be reduced, since the need is undoubtedly reduced. The same logic can be applied to, e.g., restaurant restrooms, etc.

In addition, since such sources of olfactory stimulating material are finite in size, they have to be replaced when empty, or when near empty, i.e., when a predetermined amount of the olfactory stimulating material has been dispensed. However, in a programmable dispenser that does not operate solely on a continual basis, but rather only during set periods (such as during periods of daylight or during preset hours of operation) and/or does not operate to provide a constant level of olfactory stimulating material, but rather with variable frequency or intensity, the dispensing of a predetermined amount of olfactory stimulating material, such as when the source of olfactory stimulating material is empty or near empty, can occur at different times depending on the operation of the dispenser. Accordingly, the conventional assumption that a predetermined amount of olfactory stimulating material has been dispensed after, for example, thirty days will no longer suffice.

Moreover, it is also desirable in many cases to locate the dispenser in an unobtrusive location (such as near the ceiling) for aesthetic reasons as well as to forestall tampering. In such cases, programming of the dispenser and/or determining the status of characteristics of the dispenser, such as remaining life of the refill or the batteries, is an arduous process. This is especially true when there are several, if not many, dispensers located throughout a building.

What is needed, therefore, is a dispenser which can be programmed with a great deal of flexibility in terms of times and days of operation and frequency and/or intensity of dispensing. The dispenser should also include a method for determining the dispensing of a predetermined amount of a material such as an olfactory stimulating material, which takes into consideration the variables in programming characteristics. What is also needed is a dispenser having a system that permits the remote programming of the dispenser and/or for obtaining readings of dispenser status.

BACKGROUND ART

One example of a device which does provide an indication of when an aerosol container has been emptied is provided by U.S. Pat. No. 4,063,664 to Meetze, Jr., which utilizes a counter and/or a sensor to determine evacuation of an aerosol container. In a system like that of Meetze, Jr., Muderlak and Maloney, in U.S. Pat. No. 4,830,791, make use of a timer which provides pulses at periodic intervals, a counter which counts the pulses and generates a latch signal after a predetermined number of pulses is counted (corresponding to the calculated lifetime of the odor control cartridge) and a signal activated by the latch signal. As is apparent, this Muderlak and Maloney approach cannot compensate for variations in frequency and intensity, since the device discussed operates using a predetermined "count" of pulses which are generated at a predetermined frequency, to provide the desired signal.

In a refinement on their earlier work, Muderlak and Maloney describe a system very similar to that of Meetze, Jr. whereby the number of actuations of an aerosol dispenser is counted, and an indication of the dispenser being empty is provided after 3072 actuations, in U.S. Pat. No. 5,038,972. In U.S. Pat. No. 5,126,078, Steiner, Holzner, Harunan and Owen disclose a system which uses a timer to indicate either the need for replacement of the cartridge acting as the source of material to be dispensed or replacement of the battery (which are designed to coincide) of a fan type dispenser.

A unique approach to calculating the dispensing of a predetermined amount of a material is disclosed by Dial, Chang and Huang in U.S. Pat. No. 5,772,074. In their patent, Dial et al. teach a method wherein a dispensing score representative of the time of operation of a dispenser multiplied by a factor representative of the frequency or intensity of dispensing is calculated and the calculated dispensing score is compared with a predetermined total score. Although describing a system not heretofore seen, the Dial et al. patent does not disclose a programmable dispenser in accordance with the present invention.

Unfortunately, nothing in the prior art provides a system having the flexibility to provide variations in time of operation, including start and stop times as well as days of operation and frequency and/or intensity of dispensing, whether in a fan-driven dispenser or a discrete event aerosol or pump dispenser. Moreover, nothing seen provides such a programmable dispenser which provides status indicators for characteristics such as refill and/or battery life, nor a remote programmer/status check device. The present invention provides such a system.

SUMMARY OF THE INVENTION

It is an object of the present invention to provide a dispenser for a material, wherein the dispenser is programmable with respect to operating modes such as daily start time, daily stop time, days of operation and frequency and/or intensity of operation.

It is another object of the present invention to provide a programmable dispenser for dispensing of a material which incorporates a method for indicating the status of one or more characteristics of the dispenser, such as the dispensing of a predetermined amount of the material and/or remaining life of the batteries, whereby programmed variations in dispensing time, days, frequency and/or intensity are accommodated.

It is a further object of the present invention to provide a programmable dispenser which further includes a remote device for programming the dispenser and/or for obtaining information about the status of one or more characteristics of the dispenser.

It is yet another object of the present invention to provide a programmable dispenser for an olfactory stimulating material, which can comprise in either a constant operation fan-driven dispenser, or a discrete event pump or aerosol dispenser.

It is a further object of the present invention to provide a dispenser for an olfactory stimulating material having a finite source of olfactory stimulating material, and which is powered by batteries, whereby the need to replace either the source of olfactory stimulating material or the batteries, or both, can be reliably and remotely indicated regardless of variations in dispensing time, days, frequency and/or intensity.

To overcome the deficiencies of the prior art and to achieve the objects and advantages listed above, applicants disclose, in a preferred embodiment, a programmable dispenser for a material, especially an olfactory stimulating material, which includes a source of material to be dispensed; a housing having an internal cavity sized to permit insertion thereinto of the source of material to be dispensed; an assembly for effecting dispensing of the material to be dispensed; a programmable controller in operational contact with the assembly, the programmable controller determining the time of operation and frequency and/or intensity of operation of the assembly, wherein the controller is capable of being programmed so as to set operational parameters of the dispenser including at least three of: days of the week during which the dispenser will dispense the material to be dispensed; the time during the day at which the dispenser will begin dispensing for the day; the time during the day at which the dispenser will stop dispensing for the day; and the frequency and/or intensity of dispensing.

In another preferred embodiment, applicants disclose a programmable dispenser for a material which includes a source of material to be dispensed; a housing having an internal cavity sized to permit insertion thereinto of the source of material to be dispensed; an assembly for effecting dispensing of the material to be dispensed; a programmable controller in operational contact with the assembly, the programmable controller determining the time of operation and frequency and/or intensity of operation of the assembly; and a remote control capable of communicating programming instructions to the controller.

In an especially preferred embodiment, the inventive dispenser also includes a system for indicating the status of at least one characteristic of the dispenser which is capable of indicating the dispensing of a predetermined amount of the material to be dispensed, and includes a calculator for calculating a dispensing score representative of the amount of time the dispenser is dispensing material and the frequency and/or intensity of operation; and a comparator for comparing the dispensing score with a predetermined score representative of the dispensing of a predetermined amount of the material to be dispensed and/or a system for indicating the approximate remaining life of the batteries, and includes a meter capable of measuring the charge of the batteries and a comparator for comparing the measured charge with a predetermined measurement representative of the remaining life of the batteries.

In an especially preferred embodiment, when the source of material to be dispensed has a collar, the inventive programmable dispenser further includes a fitting disposed within the housing and having a plurality of angular elements each of which define a shape generally complementary to the shape of either an inner or an outer portion of the surface of the collar, the elements cooperatively forming a shape such that either when the plurality of angular elements define a shape complementary to an inner portion of the surface of the collar, the plurality of angular elements each have a forward portion collectively defining a shape having a diameter greater than the minimum diameter of the collar and a concave portion having a diameter approximately equal to or slightly less than the minimum diameter of the collar; or when the plurality of angular elements define a shape complementary to an outer portion of the surface of the collar, the plurality of angular elements each have a forward portion collectively defining a shape having a diameter less than the maximum diameter of the collar and a concave portion having a diameter approximately equal to or slightly greater than the maximum diameter of the collar, wherein one or more of the plurality of angular elements is capable of flexing such that the fitting can be applied over the collar and thereby hold the source of material to be dispensed by the collar.

The present invention is applicable to a variety of dispensers capable of dispensing a material, such as a pesticide, an insecticide, a bactericide (i.e., a composition capable of killing airborne bacteria), but especially an olfactory stimulating material. By "olfactory stimulating material" is meant any material that affects the olfactory response to the environment of a room or like space. Such material, when dispensed in an area, performs the functions of air freshening and/or deodorizing and/or otherwise improves the smell or quality of the air in the area into which the material is dispensed.

One type of dispenser to which the present invention is applicable is a dispenser which actuates a pump or aerosol dispenser, i.e., dispensers wherein the liquid to be dispensed is contained in a container which is actuated in discrete events by an assembly which functions to depress a spray head. Although pump dispensers can technically be defined as aerosols, the two terms are being employed separately to denote non-propellant driven dispensers and propellant driven dispensers, respectively. Exemplary dispensers for pumps or aerosols are disclosed by Dial, Chang and Huang in U.S. Pat. No. 5,772,074 and by Carragan and Vecca in U.S. Pat. No. 3,589,563 (although it will be noted that the Carragan and Vecca patent is written in terms of aerosol dispensers, the same principles will apply to non-propellant driven pump dispensers). Briefly, as taught by Carragan and Vecca, an actuating arm rides on a cam. When the radius of the cam decreases, the arm moves downward, where it contacts and depresses the spray head of the aerosol (or pump) container, causing dispersal of the olfactory stimulating material. Of course, the mechanism can also work in the opposite fashion, that is, the arm is forced downward when the radius of the cam increases. Either way, dispensing of the olfactory stimulating material is accomplished in equivalent fashion.

In an alternate embodiment of an assembly for effecting dispensing of an olfactory stimulating material from an aerosol source (i.e., a suspension of olfactory stimulating material and a propellant for dispersal of the olfactory stimulating material upon actuation of the aerosol container) is the use of a solenoid and valve arrangement.

In this type arrangement, the aerosol source does not have the spray head typically associated with aerosol containers.

Rather, a solenoid is arrayed over the aerosol supply tube (discussed in more detail hereinbelow) with a valve in operational contact with the solenoid, such that constant aerosol pressure is maintained from the aerosol source, through the aerosol supply tube and to the valve. Actuation of the solenoid causes the valve to open and olfactory stimulating material to be dispensed without the mechanical cam/arm arrangements detailed above.

Another applicable type of dispenser is a fan driven dispenser, wherein the olfactory stimulating material is in liquid form, or incorporated in a gel, and the assembly for effecting dispensing is a fan which causes air to blow across or onto the material, thereby vaporizing or otherwise carrying the olfactory stimulating material along the air current and out the dispenser. The material is contained in a cup or cartridge, or other similar type of "refill" container, which is contained in the housing of the dispenser. One example of such a dispenser is that disclosed by Kunze in U.S. Pat. No. 5,370,829. In Kunze, the fan, especially a so-called squirrel-cage fan, creates air flow across the surface of the liquid or gel, causing vaporization and dispersal of the olfactory stimulating material. More particularly, such a dispenser has a housing containing at least one inlet vent and one outlet vent, a fan powered by, e.g., a battery, for directing air into and out of the vents, and a source of an olfactory stimulating material in the form of a cartridge containing a vaporizable substance (i.e., a gel incorporating the olfactory stimulating material), which is vaporized by the air flow generated by the fan and directed into the environment through the outlet vents. Due to the arrangement of the fan, vents and cartridge, the air flow is across the surface of the vaporizable substance which causes dispensing of the olfactory stimulating material.

A third dispenser which can be used with the present invention is one in which the material to be dispensed is present in a solid block of material. When heat is applied to the block, the material to be dispensed is vaporized and dispersed to the environment. Of course, the application of heat can be controlled and limited to specific times and days, and variation in the heat applied will cause variation in the intensity of dispersal.

Whether the dispenser is a fan dispenser, or an aerosol or pump dispenser (i.e., a spray head dispenser), or other type of dispenser, the dispenser comprises a housing which has an internal cavity sized to permit insertion of a source of a material to be dispensed (i.e., the cartridge in a fan dispenser and an aerosol or pump container in a spray head dispenser) and a dispensing assembly (i.e., the fan in a fan dispenser or the actuator/cam or solenoid/valve assembly in a spray head dispenser). Advantageously, the housing includes a mechanism for securing the source of material in place. That mechanism can include a magnet secured to an inner wall of the housing. A metal can (or a source of material having a metallic or metallized portion) is secured inside the housing by the action of the magnet.

The dispenser of the present invention also includes a controller for the dispensing assembly, to control the time/days and frequency and/or intensity of dispensing. The controller is most advantageously a circuit board or a computer chip or CPU (central processing unit), which contains instructions regarding programming of the dispenser, either pre-inputted or capable of being inputted by an operator. The controller also comprises a clock or timer, either internal to the controller or associated therewith. The controller is operatively connected to the dispensing assembly, such that the controller dictates when the dispensing assembly (and thus the dispenser) is operational and dispensing the olfactory stimulating material. The controller also dictates the frequency of dispensing (i.e., the number of times per day, hour, minute, etc. the assembly effects dispensing in a spray head dispenser) and/or the intensity of dispensing (i.e., the speed of the fan in a fan-driven dispenser or length of dispensing of each actuation in a spray head dispenser). The clock, once set, can set desired hours of operation, including start time and stop time (for instance, 8:00 a.m. to 6:00 p.m.), wherein the dispenser is active and dispensing during those hours of operation. The clock/controller can also determine during which days the dispenser will be operational, such that the dispenser can be operational anywhere from 0 to 7 days per week. For example, the controller can be programmed such that the dispenser is not dispensing during the weekends, or only dispensing during the weekends, or, in another embodiment, the dispenser is dispensing during different hours during the weekends than it is during the weekdays, or, in still another embodiment, the dispenser is dispensing at a different frequency and/or intensity during the weekends that it is during the weekdays.

In the alternative, the controller can comprise a light sensor (either alone or in combination with a clock/timer), such as a cadmium-sulfide photocell, which is operatively connected to the dispensing assembly such that the dispensing assembly either begins or ceases operating during periods when the ambient light is above or below certain levels.

In any event, the controller should be capable of being programmed so as to control at least three of the following dispensing characteristics: 1. days during the week in which the dispensing assembly is operational, such that the dispensing assembly can be programmed so as to be operational from 0 to 7 days per week; 2. the time during the day at which the dispenser assembly will begin dispensing for the day; 3. the time during the day at which the dispensing assembly will stop dispensing for the day; 4. the frequency and/or intensity of dispensing.

In a preferred embodiment of the intention, the controller has at least one, and most preferably a plurality, of operating modes preprogrammed into it, so the operator can simply select one of the preprogrammed modes, rather than programming the controller his- or herself. For instance, a first preprogrammed operating mode can have the dispenser operational 24 hours per day and seven days per week, dispensing in a 0.5 second burst every 30 minutes. Or, the dispenser can be preprogrammed to be operational only on weekdays (Monday through Friday), from 7:00 a.m. to 6:00 p.m., dispensing in a 0.5 second burst every 15 minutes (such as may be needed in an office building). A third preprogrammed operating mode can have the dispenser operational from Tuesday through Sunday from 5:00 p.m. to 11:00 p.m., dispensing in a 0.5 second burst every 15 minutes (such as may be needed in a restaurant). Of course, the indicated preprogrammed modes of operation are for illustrative purposes only; particular preprogrammed modes of operation can vary depending on intended use or placement. In a most preferred embodiment, the controller has three preprogrammed modes of operation.

Advantageously, the programmable dispenser of the present invention further comprises a remote control device capable of remotely providing programming instructions to the controller. The use of a remote control device can be especially advantageous when the dispenser is located in a location that precludes easy access (for aesthetic reasons as well as to prevent tampering or vandalism). For instance, it is common for dispensers of olfactory stimulating material to be located close to the ceiling in public restrooms, which means that programming without use of a remote control device necessitates use of a ladder or the like. When there are a number of such installations in a building, programming without a remote control can be a time-consuming and tedious process.

The remote control device should be capable of communicating programming instructions, i.e., instructions as to the time of day of operation of the dispenser, the days of the week during which the dispenser will be operational, and the frequency and/or intensity of dispensing, to the controller for use in controlling the dispensing assembly.

Communication of the programming instructions from the remote control device to the controller can be via any manner capable of accurately communicating the instructions. For example, the remote control device can be operatively connected to the dispenser, and the controller, via a wire or wires. This, of course, requires that the remote control device either be hard-wired into the dispenser, requiring that the remote control device be stored in the vicinity of the dispenser (such as in a lock box). Alternatively, the wiring connecting the remote control device and the dispenser can have a plug at one or both ends, with a receptacle found at either the remote device or the dispenser or both (or vice versa). This would oblige the user to either carry a length or wire around with the remote control device or store the wire with the dispenser.

In a preferred embodiment of the invention, the remote control device communicates programming instructions to the dispenser (and thus to the controller), wirelessly. For instance, the remote control device can comprise an IR (infrared) or RF (radio frequency) transmitter with the dispenser comprising a sensor capable of receiving the signals from the wireless transmitter (such as IR or RF signals) and communicate the programming instructions to the controller. The skilled artisan would be capable of selecting and assembling electronics and/or equipment, such as the circuit board and/or computer chip, capable of operating as the transmitter and sensor and thus usable in the remote control device and dispenser.

In another advantageous embodiment of the invention, the programmable dispenser also comprises a system that provides an indication of the status of at least one characteristic of the dispenser. For instance, the source of material to be dispensed, whether an aerosol or pump container for a spray head dispenser or a cartridge container for a fan-driven dispenser, is finite in capacity. This being the case, the source needs to be replaced with a fresh or full source after a certain period of operation of the dispenser. Thus, the system can provide an indication of when the source needs to be replaced, and/or the remaining life (such as in days) of the source. Similarly, although the programmable dispenser can be run via the electrical system of the building in which it is located, by either plugging into an outlet, or hard-wired into the system, most likely the programmable dispenser operates on battery power. Like the source of material to be dispensed, the battery or batteries used are finite in capacity, and need to be periodically replaced. The system that provides an indication of the status of at least one characteristic of the dispenser can therefore provide an indication that the battery or batteries need to be replaced, or the remaining life of the battery or batteries.

More particularly, since the inventive dispenser is programmable, and therefore does not operate solely on a continual basis, but rather can be set to operate during different periods (such as during preset hours of operation) and does not operate to provide a constant level of olfactory stimulating material, but rather with variable frequency or intensity, the dispensing of a predetermined amount of olfactory stimulating material, such as when the source of olfactory stimulating material is empty or near empty, can occur at different times depending on the operation of the dispenser. Accordingly, the conventional assumption that a predetermined amount of olfactory stimulating material has been dispensed after, for example, thirty days will no longer suffice.

In order to compensate for the variation in dispensing time, days or frequency and/or intensity for which the inventive dispenser is capable, a system for indicating the dispensing of a predetermined amount of the material to be dispensed, or, a system for indicating the amount of material to be dispensed which has actually been dispensed (or which remains to be dispensed) is preferably included in the programmable dispenser of the present invention. Such a system includes a timer for determining the amount of time the dispensing means is operational, a calculator for calculating a dispensing score representative of the amount of time the dispensing means is operational and the frequency and/or intensity of operation, and a comparator for comparing the dispensing score with a predetermined score representative of the dispensing of a predetermined amount of the material to be dispensed. The dispenser can also comprise signal generating means for producing a signal indicating the dispensing of the predetermined amount of the material to be dispensed when the calculated dispensing score is at least as much as a predetermined total score required for dispensing a predetermined amount of material from the source of material to be dispensed (i.e., when the refill needs to be replaced).

More specifically, in a spray head dispenser, the total dispensing time can be known. For example, in the case of a spray head container having an 80 microliter valve (i.e., a valve that dispenses 80 microliters of material for each actuation), which dispenses for 0.5 seconds during each actuation, the total amount of dispensing time can be known based on container size, such as 1440 seconds. Using this information, once the progammable dispenser is programmed, the dispensing time per day can be calculated by the calculator. Thus, if the dispenser is operational for 10 hours per day, and dispensing every 15 minutes, the calculator can multiply 10 hours per day times 4 dispensing events per hour time 0.5 seconds per dispensing event to obtain a daily dispensing score of 20 seconds. Therefore, every day the dispenser is operational at the noted rate, another 20 seconds of dispensing occurs. The comparator then can either add the daily dispensing scores together and compare the result with 1440 to determine when the source is empty and/or how many days remain before it is empty or subtract the daily dispensing scores from 1440, to determine when the source is empty, or to determine how many days of dispensing remain. (It will be seen that a dispenser operating in accordance with the noted programming will have 72 days of dispensing life (1440 seconds total/20 seconds per day); if the dispenser is only operating on weekdays, it will take 14 weeks and two days until the source needs to be replaced).

For instance, if the dispenser is operating as described above, then, for every day of operation, the comparator either adds the dispensing time (daily dispensing scores) until 1440 is reached, at which point a signal is sent to change the source of material, or it subtracts the dispensing time (daily dispensing scores) from 1440 (and then divides the result by 20) or subtracts one dispensing day from 72, to provide an indication of how many dispensing days remain (and, by extension, how many total days remain if the dispenser is not dispensing every day) and, when zero is reached, indicates that the source needs to be changed.

It will also be understood that dispensing amount (such as 80 microliters per dispensing event, multiplied by 10 hours of operation and 4 events per hour to arrive at a daily dispensing volume of 3200 microliters) can be substituted for dispensing time with the comparator comparing daily dispensing volume with total volume (or total remaining volume) of the source. Similarly, in an alternative embodiment where the dispensing program can change from day to day, the calculator calculates a different dispensing score for each day of operation.

In a fan-driven dispenser, intensity of fan operation is used in place of number of dispensing events in the same manner to provide similar information. For example, if the fan is running at x rate, the daily dispensing score is 55x (11 hours per day on Monday through Friday from 7:00 a.m. to 6:00 p.m. times x rate). If the estimated total score for dispensing a predetermined amount of the material to be dispensed is 1650x, the dispenser provides an indication that the predetermined amount of the material to be dispensed has been dispensed after 30 days of actual operation or 6 weeks of elapsed time (since the dispenser is operational only 5 days per week). Similarly, if the fan is running at rate of 2x, then the daily dispensing score in the above example will be 110x (11 hours per day times 2x), with the need to change the refill after 15 days of operation (1650x/10x).

As noted, the dispenser can provide a signal to indicate when the source needs to be changed, or to indicate other information, such as days of life remaining. The signal can take the form of a diode (i.e., a light emitting diode, or LED) or other light source, or an audible signal such as a musical tone or tones, a "beep" or a recorded voice advising the user of the dispensing of the predetermined amount of the material to be dispensed (such as a recorded voice that advises the user that it is time to replace the source of olfactory stimulating material or days of life remaining). This audible signal can be periodically repeated.

The calculator can comprise any suitable mathematical operator, such as a multiplier, which in turn is operatively connected to the assembly or programming chip. Indeed, the calculator can be built-into the chip, or comprise a separate chip or circuit. In this way, when the programming provides for a certain frequency or intensity of operation of the dispenser, the calculator will apply the appropriate factor to the time of operation provided by the system timer to arrive at the dispensing score. This adjusted time of operation can then be provided to the comparator to determine when the signal is to be generated and/or what signal to generate.

Of course, it will be recognized that the clock, timer(s), calculator, comparator and signal system, or any parts thereof, can be effected by a set of software code housed in a chip or processor unit, which thereby controls operation and signaling of the programmable dispenser of the present invention.

As noted above, the dispenser preferably provides an indication of the remaining life of any batteries used to power the dispenser. For instance, a voltage measuring circuit can be included in the dispenser, in operative contact with the batteries. When the measured voltage of the batteries falls below a certain level, a signal can be sent to advise the user to change the batteries, or indicating the remaining useful life of the batteries.

In another preferred embodiment of the invention, a remote control device is capable of querying the dispenser as to the status of the dispenser and providing an indication of that status to the user. The remote control device can be similar to that described above with respect to communicating programming instructions to the dispenser and, most advantageously, is the same remote control device (i.e., a read/send remote control).

In still another advantageous embodiment of the present invention, the housing comprises a fitting which can act in cooperation with the collar of the source of material to be dispensed (especially when the source is an aerosol container) to maintain the source in position in the housing. The fitting is disposed within the housing and has a plurality of angular elements. Each of the elements of the fitting cooperate to define a shape generally complementary to the shape of either an inner or an outer portion of the surface of the collar. In this manner, when the plurality of angular elements define a shape complementary to an inner portion of the surface of the collar, the plurality of angular elements each have a forward portion collectively defining a shape having a diameter greater than the minimum diameter of the collar and a concave portion having a diameter approximately equal to or slightly less than the minimum diameter of the collar. Similarly, when the plurality of angular elements define a shape complementary to an outer portion of the surface of the collar, the plurality of angular elements each have a forward portion collectively defining a shape having a diameter less than the maximum diameter of the collar and a concave portion having a diameter approximately equal to or slightly greater than the maximum diameter of the collar. Moreover, one or more of the plurality of angular elements is capable of flexing such that the fitting can be applied over the collar and thereby hold the source of material to be dispensed by the collar. In other words, the fitting "snaps" over the collar, with the elements cooperating to removably attach the collar, and thus the source, to the fitting.

Most advantageously, the fitting is rotatably disposed within the housing, to permit the user to rotate the source away from the housing for removal, and then "snap" a replacement into place and rotate the replacement source back into the housing. This can be accomplished by, for instance, suspending the fitting on pins journaled into either the fitting, the housing, or both, to provide the desired rotatability.

These and other objects will become more readily apparent when the following description is read in conjunction with the accompanying drawings.

DETAILED DESCRIPTION OF THE DRAWINGS

Figure 1:
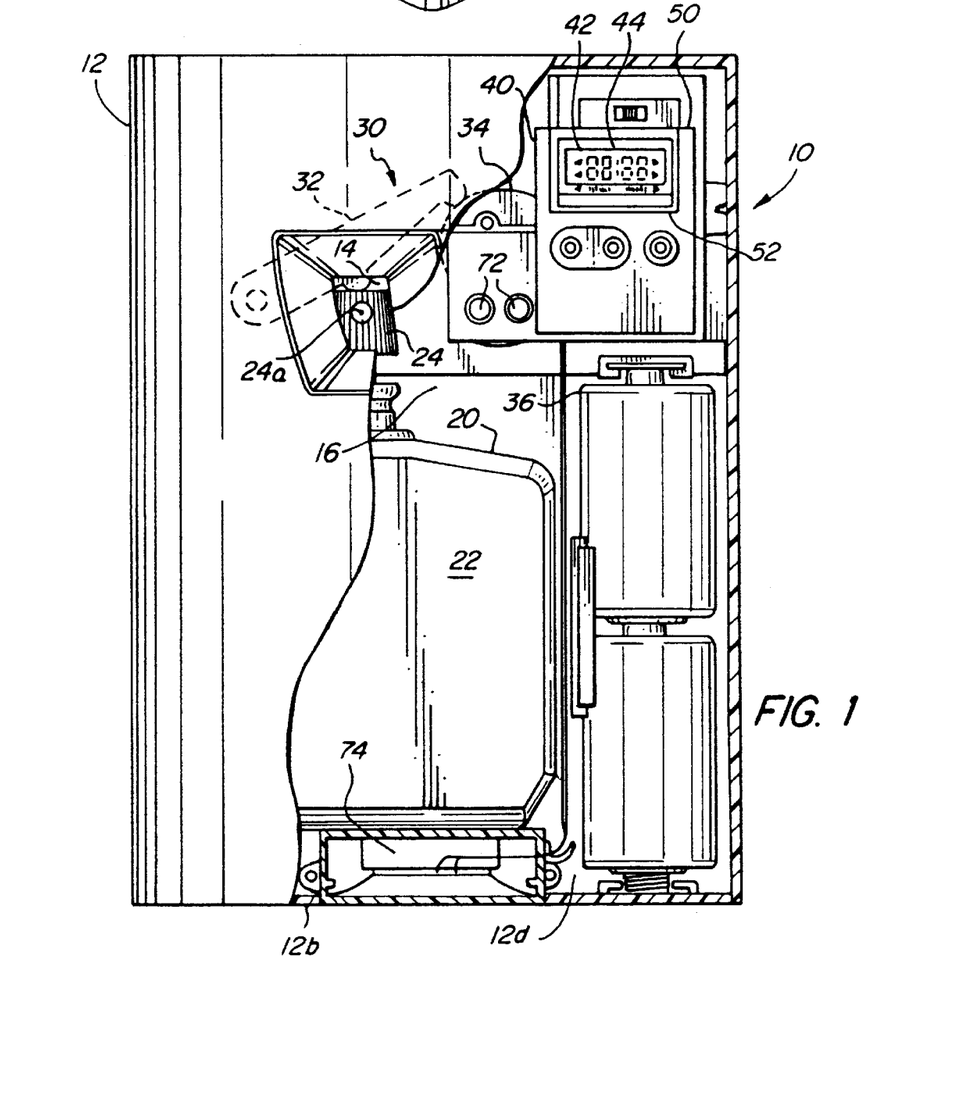
FIG. 1 is a partially broken away front plan view of a pump spray head dispenser constructed in accordance with the present invention, showing a portion of its dispensing assembly in phantom.
Figure 3:
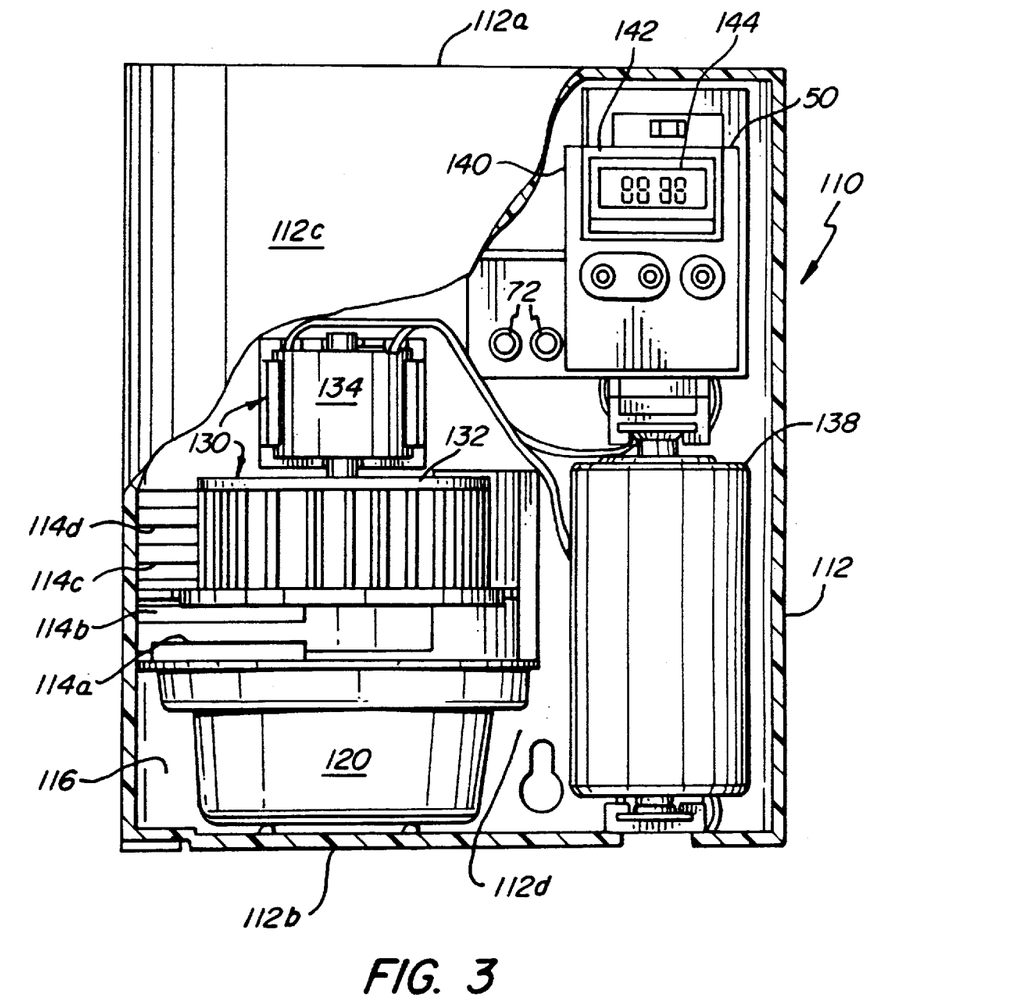
FIG. 3 is a partially broken away front plan view of a fan dispenser constructed in accordance with the present invention, showing a portion of its dispensing assembly in phantom.
Figure 4:
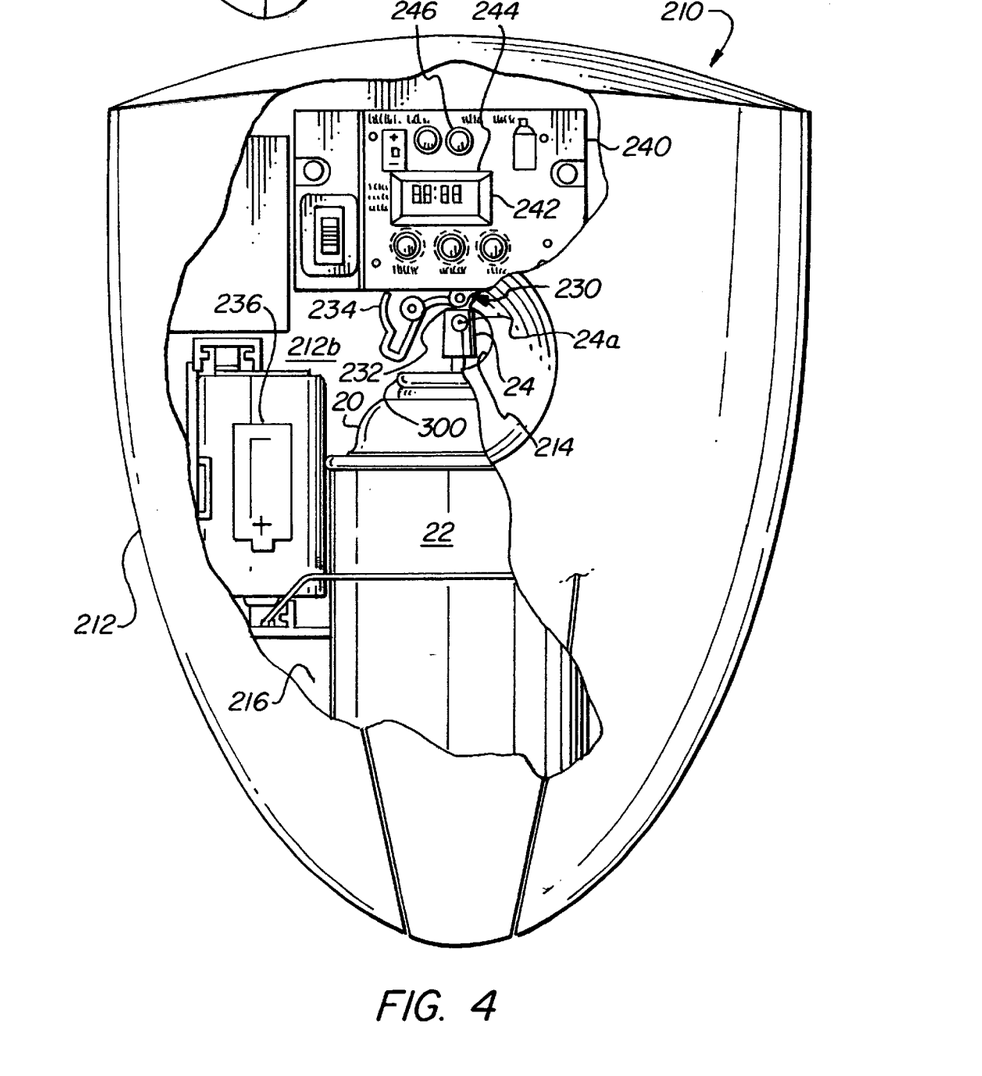
FIG. 4 is a partially broken away front plan view of an aerosol spray head dispenser constructed in accordance with the present invention, showing a portion of its dispensing assembly in phantom.

Referring to FIGS. 1, 3 and 4, dispensers, constructed in accordance with the present invention, are shown and generally designated by the reference numerals 10, 110 and 210. It should be noted that, for the sake of clarity, all the components and parts of dispensers 10, 110 and 210 may not be shown and/or marked in all the drawings. Also, as used in this description, the terms "up", "down", "front", "back", "top", "bottom", etc. refer to dispensers 10, 110 and 210 when in the orientation illustrated in FIGS. 1, 3 and 4. It will be understood, however, that dispensers 10, 110 and 210 may be in any of various orientations when in use, and, as such, the orientation illustrated in FIGS. 1, 3 and 4 is not necessary for operability.

Although this description is written in terms of dispensing an olfactory stimulating material, such description is for convenience only. It should be understood that the present invention applies to a dispenser for any dispensable material, especially a liquid (whether it be dispensed in liquid form per se, or carried in a gel or like solidifying material), such as an antistatic agent, insecticides, pesticides, bactericides, etc. By "olfactory stimulating material" is meant any material which affects the olfactory response to the environment of a room or like space. Included within the term "olfactory stimulating material" are fragrances, perfumes, deodorizing components, etc. Such materials are generally liquid in active form, i.e., when vaporized in the environment to provide olfactory stimulating effects; however, when present in dispenser 10, 110 and 210, the olfactory stimulating material may be present incorporated in a carrier medium such as an aerosol, a gel, etc.

Spray Head Dispenser

Figure 2:
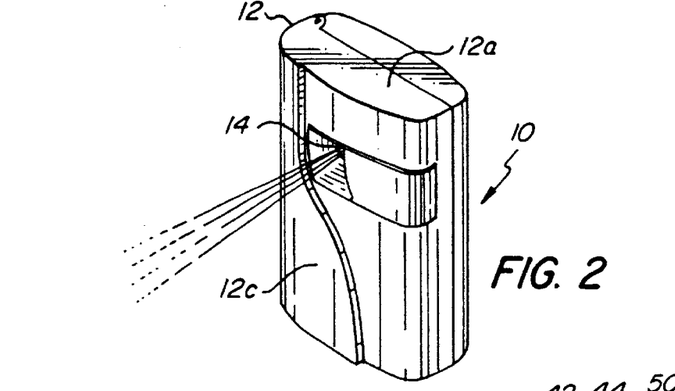
FIG. 2 is a perspective view of the spray head dispenser of FIG. 1, shown dispensing an olfactory stimulating material.
Figure 5:
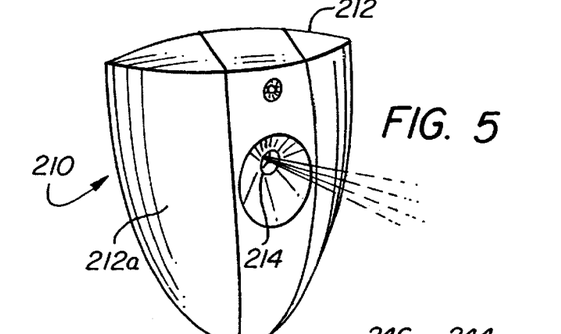
FIG. 5 is a perspective view of the spray head dispenser of FIG. 4, shown dispensing an olfactory stimulating material.

Referring now to FIG. 1, dispenser 10 generally comprises a housing 12. Housing 12 comprises a vent 14 through which olfactory stimulating material to be dispensed from a spray head dispenser can be expelled into the environment surrounding housing 12 (see FIG. 2). Housing 12 can be made of any suitable material, such as a plastic, like acrylonitrile-butadiene-styrene copolymer (ABS), low- or high-density polyethylene, polypropylene or medium impact styrene, and can be made by any suitable method, such as by injection molding. The size and shape of housing 12 is not critical, as can be seen with respect to housing 212 of dispenser 210 in FIG. 5, provided it is capable of functioning as described below.

Housing 12 includes an internal cavity 16 defined by top 12a, bottom 12b, front 12c and back 12d of housing 12. Housing 12 can stand freely on a surface or it can be mounted on a surface, such as a wall, or other vertical surface through back 12d. Desirably, front 12c is hingeably secured to housing 12, to permit opening of housing 12, and insertion of a source of olfactory stimulating material into cavity 16.

Cavity 16 of housing 12 is sized to permit insertion of an appropriate source of olfactory stimulating material therein. For instance, a spray head container 20 can be inserted into cavity 16. Spray head container 20 comprises any source of olfactory stimulating material which includes a reservoir 22 which contains the olfactory stimulating material to be dispensed, and means for dispensing the olfactory stimulating material by depressing a spray head 24. Typical among spray head containers 20 is one in which depressing spray head 24 causes olfactory stimulating material to be mechanically expelled, or pumped, through spray head orifice 24a and out vent 14. Such a pump container is illustrated in FIG. 1 with dispenser 10. Another type of spray head dispenser is one which includes a propellant material with the olfactory stimulating material in reservoir 22, under pressure, such that depressing spray head 24 forces both the olfactory stimulating material and propellant through a spray head orifice 24a and out vent 14 (214 in dispenser 210). Such containers are generally referred to as aerosol containers and are illustrated in FIG. 4 with dispenser 210. Both types of spray head containers 20 are known in the art.

Dispensers 10 and 210 also comprises a dispensing assembly 30 (230 with respect to dispenser 210), which functions to actuate spray head container 20 such that olfactory stimulating material is automatically dispensed from dispensers 10 and 210. A typical dispensing assembly 30 (and 230) is disclosed by Carragan and Vecca in U.S. Pat. No. 3,589,563 and by Dial, Chang and Huang in U.S. Pat. No. 5,772,074, the disclosures of each of which are hereby incorporated by reference herein. Such an apparatus includes an actuating arm 32 (and 232) which is biased downward by, e.g., a spring (not shown). An end of actuating arm 32 (and 232) rides along the surface of a cam 34 (and 234), which has a variable radius. Upon reaching a reduced radius portion of cam 34 (and 234), actuating arm 32 (and 232) is forced downward where it strikes and depresses spray head 24, causing dispensing of olfactory stimulating material through spray head orifice 24a and vent 14 (and 214). Cam 34 (and 234) is driven through the agency of suitable gearing and a motor (not shown), which is powered by a source of energy, such as a battery 36 (and 236).

In addition to dispensing assembly 30/230, dispensers 10 and 210 also comprise controller 40/240, which controls when dispensing assembly 30/230 causes dispensing of the olfactory stimulating material. Controller 40/240 is in operative connection with dispensing assembly 30/230, such as through a suitable circuit (not shown), and can control various aspects of dispensing assembly 30/230, including days of operation of dispensing assembly 30/230 and the hours of operation of dispensing assembly 30/230, in which case controller 40/240 comprises a clock or timer 42/242 and/or a light sensor (not shown); and the frequency of actuation of spray head 24 by actuating arm 32/232, in which case controller 40/240 makes use of clock or timer 42/242, which sends pulses triggering dispensing assembly 30/230 to dispense olfactory stimulating material at certain intervals. Suitable controllers 40/240 for controlling dispensing assembly 30/230 would be readily ascertainable by the skilled artisan and include computer chips and circuit boards, and other known types of electronic circuits.

Fan Dispenser

Like dispensers 10 and 210, dispenser 110 generally comprises a housing 112. Housing 112 comprises at least one, and most commonly a plurality of vents 114*a*, 114*b*, 114*c*, 114*d*, etc., which comprise inlet vents 114*a*, 114*b* and outlet vents 114*c*, 114*d*. Housing 112 can be made of any suitable material, such as a plastic, like ABS, low- or high-density polyethylene, polypropylene or medium impact styrene, and can be made by any suitable method, such as by injection molding.

Housing 112 includes an internal cavity 116 defined by top 112*a*, bottom 112*b*, front 112*c* and back 112*d* of housing 112. Housing 112 can stand freely on a surface or it can be mounted on a surface, such as a wall, or other vertical surface through back 112*d*. Desirably, front 112*c* is hingeably secured to housing 112, to permit opening of housing 112, and insertion of a source of olfactory stimulating material into cavity 116.

Cavity 116 of housing 112 is sized to permit insertion of an appropriate source of olfactory stimulating material therein. For instance, a cartridge 120 can be inserted into cavity 116. Cartridge 120 comprises a housing 122 which has a reservoir which contains the olfactory stimulating material to be dispensed by dispenser 110, either in its liquid form, or incorporated in a suitable carrier agent, such as a gel. Whether the olfactory stimulating material is present as a liquid or incorporated in a gel, dispensing occurs when air flows across the surface of the olfactory stimulating material, vaporizing the material, and carrying out into the environment with the air.

Dispenser 110 also comprises a dispensing assembly 130, which creates an air flow across the surface of the olfactory stimulating material in cartridge 120. A typical dispensing assembly 130 is disclosed by Kunze in U.S. Pat. No. 5,370,829, the disclosure of which is hereby incorporated by reference herein. Such an apparatus includes a fan 132, which creates a flow of air in inlet vents 114*a*, 114*b* across the surface of olfactory stimulating material in cartridge 120 and out outlet vents 114*c*, 114*d*. Fan 132 is driven through the agency of suitable gearing and a motor 134, which is powered by a source of energy, such as a battery 138.

Like dispenser 10 (and 210), dispenser 110 also comprises controller 140, which controls when dispensing assembly 130 causes dispensing of the olfactory stimulating material. Controller 140 is in operative connection with dispensing assembly 130, such as through a suitable circuit (not shown), and can control various aspects of dispensing assembly 130, including the days and hours of operation of dispensing assembly 130, in which case controller 140 comprises a clock or timer 142 and/or a light sensor (not shown); and the intensity of operation of fan 132. Suitable controllers 140 for controlling dispensing assembly 130 are known in the art.

Figure 8:
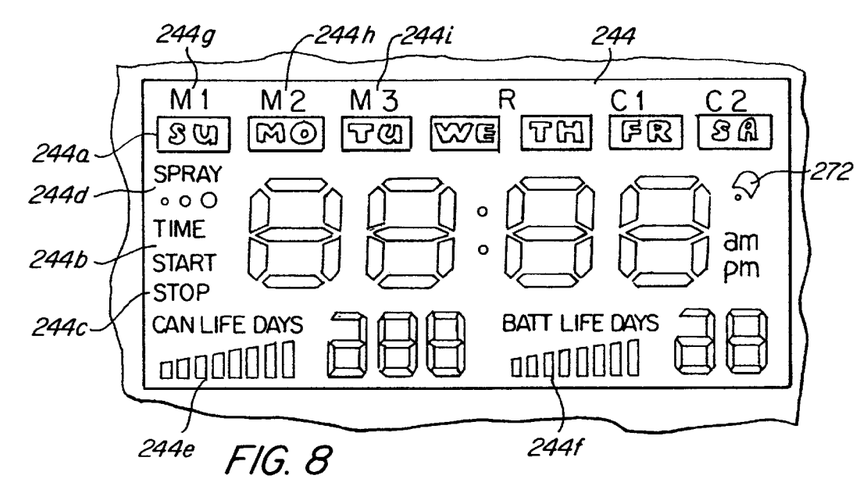
FIG. 8 is a front view of a display panel from the dispensers of FIGS. 1 and 4 and/or the remote control device of FIG. 6.

Dispensers 10, 110 and 210 each preferably include a display 44 (and 144 and 244). The display 44 (and 144 and 244) can include different information depending on the programmability of the respective dispenser. For instance, if dispensers 10, 110 and 210 can only be programmed by time during the day at which dispensing begins and ends operation and frequency and/or intensity of dispensing, display 44 need not be complex. However, where dispensers 10, 110 or 210 can be programmed by the above, plus, for example, days of the week, or where preprogrammed modes of operation are possible, or where the status of the dispenser can be indicated, display 44/144/244 can display all the indicated information, as shown in FIG. 8. As can be seen, display 244 can indicate days of the week 244*g*, "time start" 244*b*, "time stop" 244*c*, spray frequency 244*d*, can life (in days) 244*e*, battery life (in days) 244*f*, and preprogrammed modes of operation M1, M2 and M3, 244*g*, 244*h*, 244*i*. Of course, the practitioner will recognize other information that can be displayed by display 44/144/244.

Figure 6:
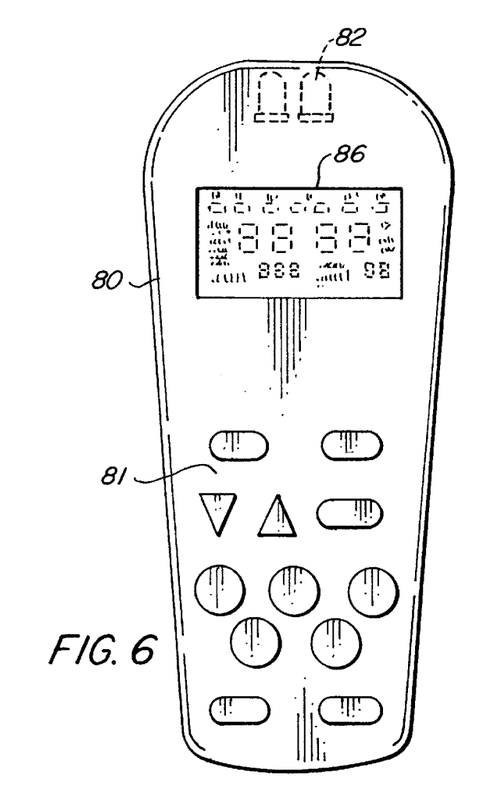
FIG. 6 is a front plan view of a remote control device useful in conjunction with the dispensers of FIGS. 1–5.
Figure 7:
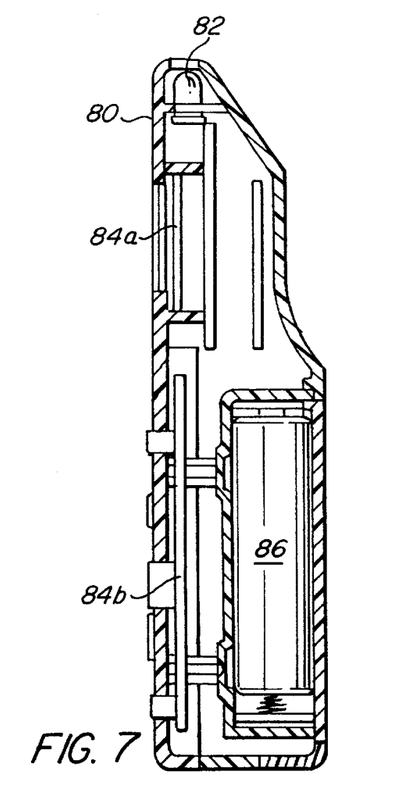
FIG. 7 is a side cross-sectional view of the remote control device of FIG. 6.

As noted, and referring to FIGS. 6 and 7, a remote control device 80 can also be used in conjunction with dispenser 10, 110 and/or 210. Such a remote control device 80 is preferably powered by one or more batteries 86 and can be based on IR or RF communications, or another communication protocol (including a wire) capable of establishing communication between remote 80 and dispenser 10, 110 and/or 210. Most commonly, remote control 80 will use IR communication protocols, and include an IR signal node 82. Device 80 will also most preferably incorporate one or more circuit boards 84*a*, 84*b*, etc. to permit inputting of programming instructions in cooperation with display 86 (which can take the form of display 44 or display 46 discussed above). Circuit boards 84*a*, 84*b*, etc. can accept input from remote control device keypad 81 and communicate the programming instructions input thereby to programmable dispenser 10, 110 and/or 210 through, e.g., sensor 246; more specifically, the programming instructions are communicated to controller 40/140/240 of the dispensers.

In the alternative, remote control device 80 can be used to query dispensers 10, 110 and/or 210 to obtain information from the dispensers, such as "can" life (that is, whether the source of material needs to be replaced and/or how many days remain before the source of material needs to be replaced) and/or battery life, with the information displayed on display 86. Most preferably, remote control device 80 can function both as a programmer for dispensers 10, 110 and/or 210, and to query the dispensers as to status (i.e., read/send).

Although there is no criticality to the particular assignment of keys in keypad 81, they can include keys to increment the programming characteristic being acted on, such as time, days of the week and/or frequency and/or intensity of operation; mode keys to input preprogrammed modes of operation; selection keys to select the programming characteristic to adjust; time/day or date set key; can/battery reset key for when the source and/or batteries are replaced; read keys to read status information from the dispenser; even a lock/unlock key to lock or unlock the front 12*c* of housing 12.

Figure 11A:
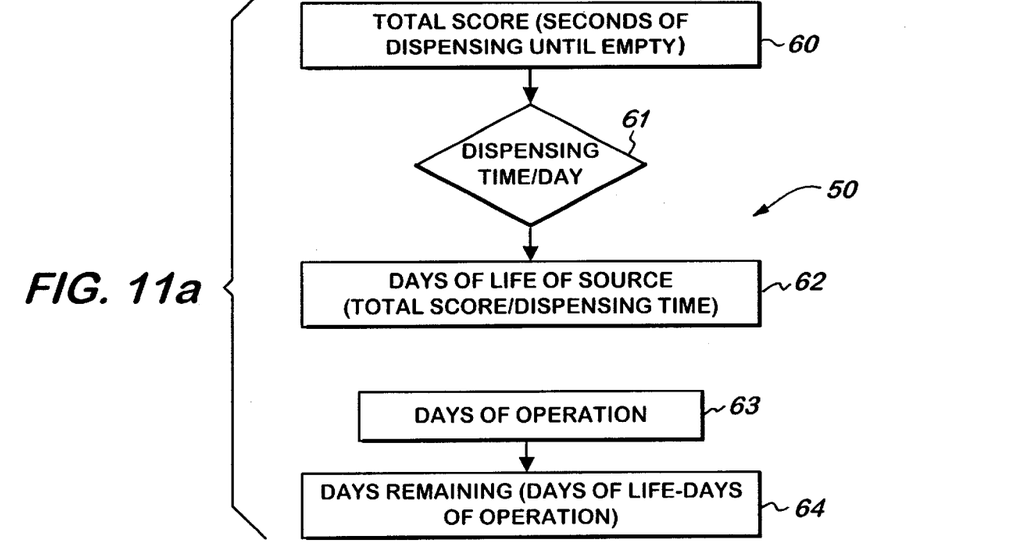
FIG. 11a is a functional block diagram illustrating one process for determining and indicating of the dispensing of a predetermined amount of a material from the dispensers of FIGS. 1 and 4.
Figure 11B:
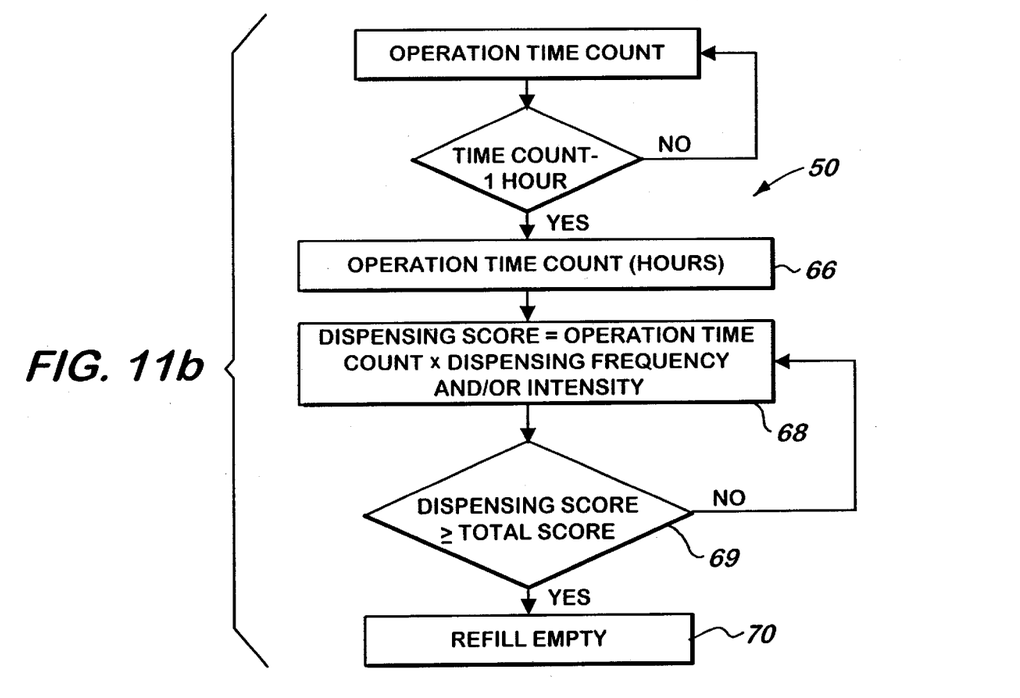
FIG. 11b is a functional block diagram illustrating one process for determining and indicating of the dispensing of a predetermined amount of a material from the dispensers of FIGS. 1 and 4.

As noted, dispensers 10, 110 and 210 preferably include a system 50 for determining that a predetermined amount of the olfactory stimulating material has been dispensed, in order to provide an indication that the source of material needs to be replaced and/or of days remaining before the source needs to be replaced. Although system 50 can function mechanically, it is most preferably run pursuant to a software code incorporated into a chip or processor 52 which may provide instructions for controllers 40, 140 and 240, as well as clock or timer 42, 142 and 242. FIGS. 11*a* and 11*b* are functional block diagrams depicting systems 50 for providing an indication that a predetermined amount of the olfactory stimulating material has been dispensed. By "predetermined" amount of the olfactory stimulating material is meant any amount after which it is desired that there be an indication of that amount having been dispensed. Most commonly, the predetermined amount will be the amount of olfactory stimulating material present in spray head container 20 or cartridge 120, thus providing an indication that spray head container 20 or cartridge 120 is empty or near empty and needs to be replaced, and/or days remaining before replacement is necessary.

Referring to FIG. 11a, a total score is first computed, corresponding to a time count for each dispensing intensity and/or frequency until the source of material is empty 60. That total score is then divided by the dispensing time per day at the programmed settings 61 to arrive at the total number of days of life of the source 62. For instance, if dispenser 10 and/or 210 dispenses for 0.5 seconds at each actuation (based on the valve size), and is programmed to dispense four times per hour and eleven hours per day (such as 8:00 a.m. to 7:00 p.m.), then the dispensing time per day at the programmed settings is 0.5 seconds×4 times per hour×11 hours per day=22 seconds per day. If the source has a useful life of 1440 seconds, then the days of can life is 1440/22=65 (rounded down to the next whole number).

Next, a count is maintained for each day of operation 63, and for each day, a day is subtracted from the days of life of the source (either directly or by subtracting 22 seconds from 1440, then 22 from 1418, then 22 from 1396, etc.) to provide days of source life remaining 64. When this number is 0, a signal is sent that the source needs to be replaced 65. In the alternative, illustrated in FIG. 11b, an operation time count can be maintained 66, corresponding to the hours (or other unit) of time dispenser 10, 110 and/or 210 is operational. The dispensing intensity and/or frequency 67 is then used to calculate a dispensing score 68 by, for instance, multiplying the operation time count 66 by a multiplier representative of the frequency or intensity of dispensing 67. For instance, if a standard is adopted as a dispensing frequency of one 0.5 second actuation every fifteen minutes, the hourly operation time count is multiplied by 2 second (4 actuations per hour times 0.5 seconds per actuation). Each of the multiplied operation time counts is added to provide the dispensing score 69. The dispensing score 69 is then compared to the total score 68, which represents the score when the predetermined amount of olfactory stimulating material has been dispensed, and when the dispensing score is greater than or equal to the total score, a signal is generated 70, indicative of the dispensing of a predetermined amount of the olfactory stimulating material. The total score can be determined in several ways, each readily ascertainable by the skilled artisan. One method of determining the total score is to determine the number of hours it takes to dispense a predetermined amount of the olfactory stimulating material at the frequency or intensity which is used as the standard, that is, the frequency or intensity which is multiplied by 1. This total score can then be used, against which the dispensing score is compared.

The generation of a signal indicative of the fact that the predetermined amount of the olfactory stimulating material has been dispensed can be made in any of several ways. For instance, a circuit (not shown) can be used to illuminate one or more light emitting diodes 72, or other light sources upon direction from the processor, either on dispenser 10, 110 and/or 210, or on remote 80. Alternatively, or in addition, a speaker 74 or other like means can be used to provide an audible signal, such as a musical tone or tones, a "beep" or a voice providing an indication of the dispensing of a predetermined amount of the olfactory stimulating material, upon direction from processor 52 through an appropriate circuit (not shown). The circuits which can be employed for illuminating a diode or providing directions to produce an audible signal will be familiar to the skilled artisan.

Although, as noted, system 50 can be operated by the use of a single software code present in processor 52, it will be understood that the individual functions of system 50 can be separately effected, either electronically, mechanically, or by the provision of separate processors having individual responsibility, as would be familiar to the skilled artisan upon review of this description. In addition, the precise logic to be used to indicate the days of source life remaining, or the need to replace the source, can vary widely and is not restricted to the foregoing. Similar logic can be used to provide an indication of battery life remaining.

Figure 9:
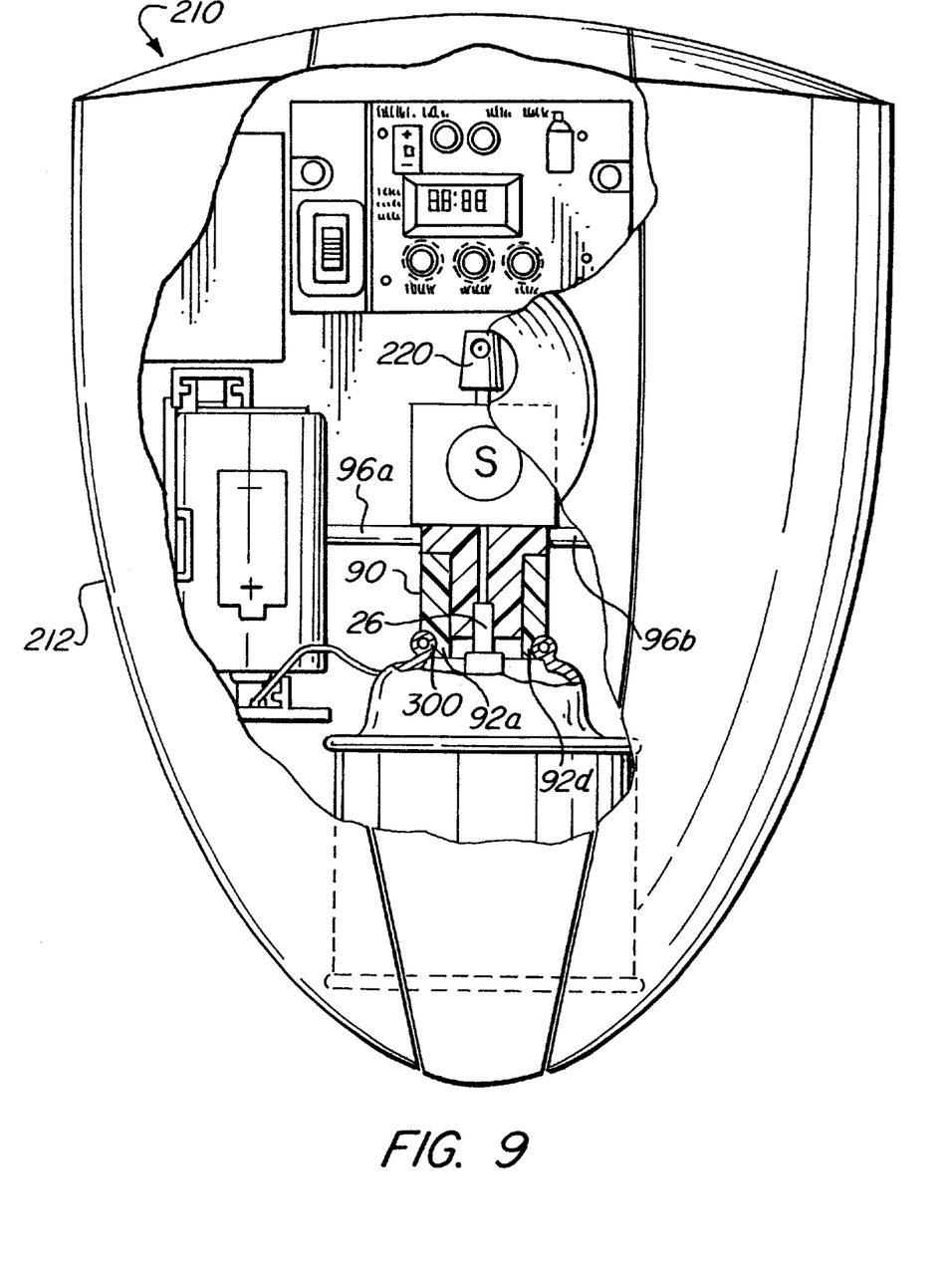
FIG. 9 is a partially broken away front plan view of an alternate embodiment of an aerosol spray head dispenser constructed in accordance with the present invention.
Figure 10:
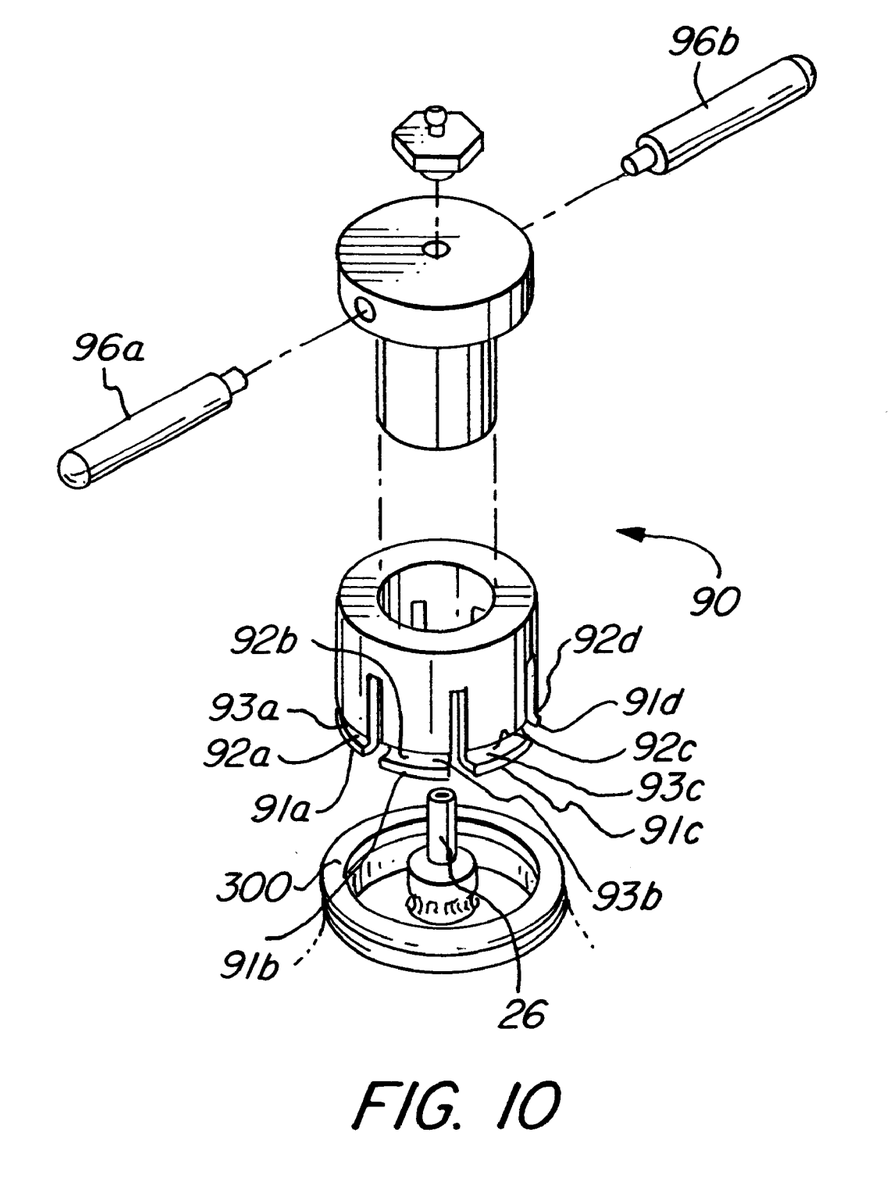
FIG. 10 is a partially exploded perspective view of a fitting used in the dispenser of FIG. 9 to maintain an aerosol can in position.

Referring now to FIG. 10, in still another advantageous embodiment of the present invention, housing 12 comprises a fitting 90 which can act in cooperation with the collar 300 of the source of material to be dispensed (especially when the source is a spray head source 20, such as an aerosol can) to maintain the source in position in housing 12. Fitting 90 is disposed within housing 12 and has a plurality of angular elements 92a, 92b, 92c, 92d, etc. Each of elements 92a, 92b, 92c, 92d, etc. of fitting 90 cooperate to define a shape generally complementary to the shape of either an inner or an outer portion of the surface of the collar 300 (usually, collar 300 is circular in shape, as illustrated in FIG. 10). In this manner, when the plurality of angular elements 92a, 92b, 92c, 92d, etc. define a shape complementary to an inner portion of the surface of the collar 300, the plurality of angular elements 92a, 92b, 92c, 92d, etc. each have a forward portion 91a, 91b, 91c, 91d, etc. collectively defining a shape having a diameter greater than the minimum diameter of the collar 300 and a concave portion 93a, 93b, 93c, 93d, etc. having a diameter approximately equal to or slightly less than the minimum diameter of the collar 300. In use, fitting 90 "snaps" over the collar 300, as illustrated in FIGS. 9 and 10, with the elements 92a, 92b, 92c, 92d, etc. cooperating to removably attach the collar 300, and thus the source 20, to fitting 90 and thus to housing 12.

Most advantageously, and as seen in FIG. 9, fitting 90 is rotatably disposed within housing 12, to permit the user to rotate source 20 away from housing 12 for removal, and then "snap" a replacement into place and rotate the replacement source back into housing 12. This can be accomplished by suspending fitting 90 on pins 96a, 96b journaled into either fitting 90, housing 12, or both, to provide the desired rotatability.

As also illustrated in FIGS. 9 and 10, dispenser 210 can comprise a solenoid "S" in combination with a valve 220, to replace assembly 230. Solenoid "S" is disposed over aerosol supply tube 26 (i.e., as in a standard aerosol can from which the depressible spray head 24 has been removed), such that an open connection exists between aerosol reservoir 22 and valve 220, with Solenoid S therebetween. Solenoid S can be operatively connected to controller 40 and permit valve 220 to open and dispense the material to be dispensed at times and frequencies determined by controller 40, thus eliminating the need to a complex mechanical arrangement. As can be seen in FIGS. 9 and 10, solenoid S can cooperate with fitting 90 to provide an attachment/dispensing function which is flexible and reliable.

It should be understood by those skilled in the art that obvious modifications can be made to the present invention without departing from the spirit of the invention. Accordingly, reference should be made primarily to the accompanying claims, rather than the foregoing specification, to determine the scope of the invention.

What is claimed is:

1. A programmable dispenser for a material, comprising:
 a source of material to be dispensed;
 a housing having an internal cavity sized to permit insertion thereinto of the source of material to be dispensed;

an assembly for dispensing the material to be dispensed;

a programmable controller in operational contact with the assembly, the programmable controller determining the time of operation and frequency and/or intensity of operation of the assembly, wherein the controller is capable of being programmed so as to set, for the dispenser, operational parameters selected from the group consisting of: days of the week during which the material will be dispensed, the time during the day at which the dispenser will begin dispensing for the day, the time during the day at which the dispenser will stop dispensing for the day, and the frequency and/or intensity of dispensing;

wherein the dispenser provides a daily "day count" indicative of the number of days remaining for which there is material to be dispensed, the first day "day count" being computed from:
  (a) an initial determination of a total score representative of the total amount of material available to be dispensed;
  (b) dividing the total score by the dispensing time per day for a selected set of operational parameters; and
  (c) rounding the resulting quotient down to the next whole number;

and wherein the "day count" for a successive day is computed from:
  (a) subtracting, from the total score, the dispensing time per day from the previous day, so as to compute a new "total score;"
  (b) dividing the new total score by the dispensing time for a successive day for a selected set of operational parameters; and
  (c) rounding the resulting quotient down to the next whole number.

2. The dispenser of claim 1, wherein the material to be dispensed comprises an olfactory stimulating material, an insecticide, a pesticide or a bactericide.

3. The dispenser of claim 1, wherein the source of material to be dispensed comprises a spray head dispenser.

4. The dispenser of claim 3, wherein the spray head dispenser comprises a depressible spray head and the assembly comprises an actuator for depressing the spray head in response to the controller.

5. The dispenser of claim 3, wherein the spray head dispenser comprises an aerosol can and the assembly comprises a solenoid/valve assembly wherein the solenoid is in operational connection with both the valve and the aerosol dispenser to dispense the material to be dispensed in response to the controller.

6. The dispenser of claim 1, wherein the controller further comprises at least one preprogrammed mode of operation of the dispenser.

7. The dispenser as claimed in claim 1, wherein the dispenser further comprises a remote control capable of remotely communicating programming instructions to the controller, the remote control itself comprising a display for displaying the "day count".

8. The dispenser as claimed in claim 1, wherein the dispenser further comprises a display for displaying the "day count".

9. The dispenser as claimed in claim 1, wherein the total score is determined by the number of hours it takes to dispense a predetermined amount of the material to be dispensed at a predetermined frequency or intensity.

10. A method of determining the how many days of dispensing are available in a source of material to be dispensed, the source of material being housed in an internal cavity of a dispenser, the dispenser comprising an assembly for dispensing the material to be dispensed, a controller, operatively coupled to the assembly, for determining the time of operation and frequency and/or intensity of operation of the assembly, wherein the controller includes operational parameters selected from the group consisting of: days of the week during which the material will be dispensed, the time during the day at which the dispenser will begin dispensing for the day, the time during the day at which the dispenser will stop dispensing for the day, and the frequency and/or intensity of dispensing; wherein the method of providing a "day count" indicative of the number of days remaining for which there is material to be dispensed comprises the steps of:

determining a total score representative of the total amount of material available to be dispensed; and for the first day that the dispenser is operational:
  (a) dividing the total score by the dispensing time per day for a selected set of operational parameters; and
  (b) rounding the resulting quotient down to the next whole number;

for each successive day that the dispenser is operational:
  (a) subtracting, from the total score, the dispensing time per day from the previous day, so as to compute a new "total score;"
  (b) dividing the new total score by the dispensing time for a successive day for a selected set of operational parameters; and
  (c) rounding the resulting quotient down to the next whole number.

11. The method as claimed in claim 10, including the step of displaying the "day count" on a display on the dispenser.

12. The method as claimed in claim 10, including a remote control operatively coupleable to the dispenser; wherein the method comprises the further step of displaying the "day count" on a display on the remote control.

* * * * *